United States Patent
Kokubo et al.

(10) Patent No.: US 9,334,214 B2
(45) Date of Patent: May 10, 2016

(54) LONG-CHAIN ALKYL-ETHERIFIED FULLERENE DERIVATIVE, PRODUCTION METHOD FOR THE SAME, AND RESIN COMPOSITION USING THE SAME

(71) Applicant: TOTAI CO., LTD., Tokyo (JP)

(72) Inventors: Ken Kokubo, Suita (JP); Akio Harada, Kyoto (JP); Takeshi Noguchi, Yufu (JP)

(73) Assignee: TOTAI CO., LTD., Tokyo (JP)

( * ) Notice: Subject to any disclaimer, the term of this patent is extended or adjusted under 35 U.S.C. 154(b) by 0 days.

(21) Appl. No.: 14/755,218

(22) Filed: Jun. 30, 2015

(65) Prior Publication Data
US 2016/0009620 A1    Jan. 14, 2016

(30) Foreign Application Priority Data

Jul. 10, 2014    (JP) ................................ 2014-142491

(51) Int. Cl.
| | |
|---|---|
| *C08K 9/00* | (2006.01) |
| *C07C 43/20* | (2006.01) |
| *C07C 41/01* | (2006.01) |
| *C08K 5/06* | (2006.01) |

(52) U.S. Cl.
CPC ................. *C07C 43/20* (2013.01); *C07C 41/01* (2013.01); *C08K 5/06* (2013.01)

(58) Field of Classification Search
CPC ................................... C01B 3/00; C07C 29/58
See application file for complete search history.

(56) References Cited

U.S. PATENT DOCUMENTS

| | | | | |
|---|---|---|---|---|
| 8,957,261 B2 * | 2/2015 | Kokubo | .............. | C01B 31/0213 568/812 |
| 8,987,526 B2 * | 3/2015 | Kokubo | .............. | C01B 31/0213 568/817 |
| 2005/0221184 A1 * | 10/2005 | Naruto | .................. | H01M 4/133 429/231.8 |

FOREIGN PATENT DOCUMENTS

| | | |
|---|---|---|
| JP | 2014-172865 A | 9/2014 |
| RU | 2 384 561 C2 | 3/2010 |

OTHER PUBLICATIONS

Wan et al., "The Rheological, Thermostable, and Mechanical Properties of Polypropylene/Fullerene C60 Nanocomposites With Improved Interfacial Interaction", Polymer Engineering and Science, 2012, pp. 1457-1463.
Zhao et al., "Thermal Stability and Rheological Behaviors of High-Density Polyethylene/Fullerene Nanocomposites", Journal of Nanomaterials, 2012, Article ID 340962, pp. 1-6.
Yang et al., "Synthesis and Reactivity of 2H-Pyran Moiety in [60] Fullerene Cage Skeleton," The Journal of Organic Chemistry, 2010, vol. 75, No. 13, pp. 4567-4573.
Borghi et al., "Photolysis of Dialkoxy Disulfides: A Convenient Source of Alkoxy Radicals for Addition to the Sphere pf Fullerene C60," The Journal of Organic Chemistry, 1996, vol. 61, No. 10, pp. 3327-3331.
Cremonini et al., "Addition of Alkylthio and Alkoxy Radicals to C60 Studied by ESR," The Journal of Organic Chemistry, 1993, vol. 58, No. 17, pp. 4735-4738.

* cited by examiner

*Primary Examiner* — Hannah Pak
(74) *Attorney, Agent, or Firm* — Westerman, Hattori, Daniels & Adrian, LLP

(57) ABSTRACT

Provided is a resin composition having excellent heat resistance by virtue of improved compatibility of a fullerene with a resin. Specifically, provided is a long-chain alkyl-etherified fullerene derivative, including: a fullerene skeleton formed of a spherical shell-shaped carbon molecule; and a long-chain alkyl group having 4 or more carbon atoms, which is bonded to the fullerene skeleton through an ether bond.

7 Claims, 3 Drawing Sheets

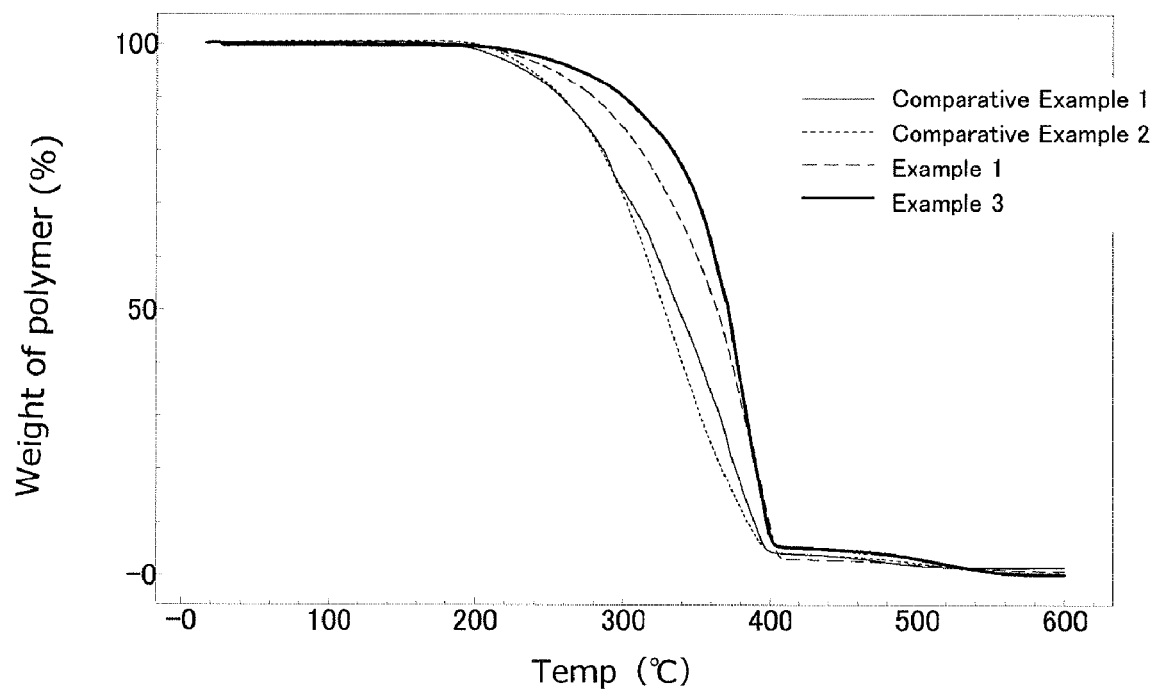

LONG-CHAIN ALKYL-ETHERIFIED FULLERENE DERIVATIVE, PRODUCTION METHOD FOR THE SAME, AND RESIN COMPOSITION USING THE SAME

BACKGROUND

1. Field of the Invention

The present invention relates to a long-chain alkyl-etherified fullerene derivative, a production method for the same, and a resin composition using the same, and more particularly, to a resin composition having excellent heat resistance by virtue of improved compatibility of a long-chain alkyl-etherified fullerene derivative with a resin.

2. Description of the Related Art

In recent years, a large amount of research has been conducted to improve heat resistance of a resin by adding a fullerene ($C_{60}$). For example, a polypropylene or high-density polyethylene resin composition containing the fullerene ($C_{60}$) is disclosed in D. Wan, et al., "The Rheological Thermostable and Mechanical Properties of Polypropylene/Fullerene $C_{60}$ Nanocomposites with Improved Interfacial Interaction", Polym. Eng. Sci., 2012, 1457-1463 or L. Zhao, et al., "Thermal Stability and Rheological Behaviors of High-Density Polyethylene/Fullerene Nanocomposites", J. Nanomater., 2012, Article ID 340962, 1-6.

However, in order to homogeneously disperse the fullerene, it is necessary to mix the fullerene and the resin over a long period of time under a state in which the resin is melted at about 200° C. When the fullerene is not sufficiently dispersed, the heat resistance is not improved, and besides, an aggregate of the fullerene reduces light transmittance. Accordingly, it has been desired to develop a fullerene derivative, which is easily mixed with the resin in order to more simply improve the heat resistance and transparency.

However, solvents in which the fullerene ($C_{60}$) disclosed in D. Wan, et al. and in L. Zhao, et al., dissolves are substantially limited to aromatic solvents, and the fullerene does not dissolve at all in non-polar solvents such as hexane. Accordingly, compatibility of the fullerene ($C_{60}$) with a non-polar resin such as polyethylene or polypropylene (oil solubility) is insufficient. Consequently, part of the fullerene ($C_{60}$) remains as an aggregate in the mixed resin, and a function of the fullerene (such as a radical scavenging effect) has not been able to be exhibited in a fully effective manner. In addition, when the resin composition is formed into a film or a resin molding, the aggregate is present on its surface or in its inside, which may cause various problems in practical use, such as reductions in transparency and mechanical strength.

In addition, the improvement in heat resistance of the resin composition has been desired in each of the following applications: food packaging materials, molding materials, automobile-related materials, electrical and electronic equipment-related materials, building materials, and industrial machinery-related materials. When heat resistance of each of those materials can be improved with the resin composition containing the fullerene, further industrial development can be facilitated.

SUMMARY

In view of the above-mentioned background, a resin composition having excellent heat resistance by virtue of improved compatibility of a fullerene with a resin is provided.

To achieve the above-mentioned matter, a first aspect resides in a long-chain alkyl-etherified fullerene derivative, including: a fullerene skeleton formed of a spherical shell-shaped carbon molecule; and a long-chain alkyl group having 4 or more carbon atoms, which is bonded to the fullerene skeleton through an ether bond.

In addition, a second aspect resides in a production method for the long-chain alkyl-etherified fullerene derivative of the first aspect, including: a first step of synthesizing a polycyclosulfated fullerene (CS) from a fullerene and fuming sulfuric acid; and a second step of synthesizing the long-chain alkyl-etherified fullerene derivative by introducing the long-chain alkyl group to the fullerene skeleton through the ether bond generated by reacting the polycyclosulfated fullerene (CS) with a long-chain alcohol.

Further, a third aspect resides in a resin composition, including a resin and the long-chain alkyl-etherified fullerene derivative of the first aspect.

That is, the inventors of the present invention have conducted extensive investigations in order to solve the above-mentioned problem, and during the course of the investigations, the inventors have conceived, with a view to improving compatibility between a resin and a fullerene, that when a fullerene, which is easily compatible with a non-polar solvent, which has heretofore been difficult, can be invented, the compatibility between the resin and the fullerene may be improved. With this in mind, the inventors have conducted further research. As a result, the inventors have found that a fullerene derivative, which is compatible with a non-polar solvent, is obtained by introducing a long-chain alkyl group to a fullerene skeleton through an ether bond.

As described above, the first aspect is the long-chain alkyl-etherified fullerene derivative, including: the fullerene skeleton formed of a spherical shell-shaped carbon molecule; and the long-chain alkyl group having 4 or more carbon atoms, which is bonded to the fullerene skeleton through an ether bond. Thus, the compatibility of the long-chain alkyl-etherified fullerene derivative with the resin can be improved, and hence the resin composition having excellent heat resistance is obtained.

In addition, when a hydroxy group is further bonded to the fullerene skeleton, not only effects such as an antistatic effect and a dew condensation-preventing effect are obtained by virtue of an amphiphilic property, but also the hydroxy group, which is bonded to the n-conjugated system of the fullerene and is weakly acidic, is considered to have a radical scavenging effect like hydroxy groups of polyphenols and hydroquinones as antioxidants. Thus, a contribution is made to the improvement in heat resistance of the resin composition.

Further, when the ratio of the number of the long-chain alkyl groups bonded to the fullerene skeleton to the number of the hydroxy groups bonded to the fullerene skeleton (number of long-chain alkyl groups/number of hydroxy groups) is from 1/1 to 9/1, a contribution is made to the improvement in the heat resistance without the impairment of the compatibility with the resin.

When the production method for the above-mentioned long-chain alkyl-etherified fullerene derivative, including: the first step of synthesizing a polycyclosulfated fullerene (CS) from a fullerene and fuming sulfuric acid; and the second step of synthesizing the long-chain alkyl-etherified fullerene derivative by introducing the long-chain alkyl group to the fullerene skeleton through the ether bond generated by reacting the polycyclosulfated fullerene (CS) with a long-chain alcohol is adopted, a desired fullerene derivative is obtained by a simpler method.

In addition, a resin composition, containing: a resin; and the long-chain alkyl-etherified fullerene derivative is further excellent in heat resistance.

When the content of the long-chain alkyl-etherified fullerene derivative is from 0.01 part by weight to 10 parts by weight with respect to 100 parts by weight of the resin, the resin composition becomes excellent in heat resistance more effectively with a low content of the long-chain alkyl-etherified fullerene derivative.

When the resin includes at least one resin selected from the group consisting of a crystalline thermoplastic resin, a non-crystalline thermoplastic resin, and a curable resin, the heat resistance of the resin composition can be enhanced, and hence the heat resistance of a resin molding to be obtained from the resin composition can be enhanced as well.

BRIEF DESCRIPTION OF THE DRAWINGS

FIG. 3 is a graph for showing the heat resistances (TGA measurement results) of octyl-etherified fullerene derivative/polypropylene nanocomposites.

DETAILED DESCRIPTION OF THE PREFERRED EMBODIMENTS

Figure 1:
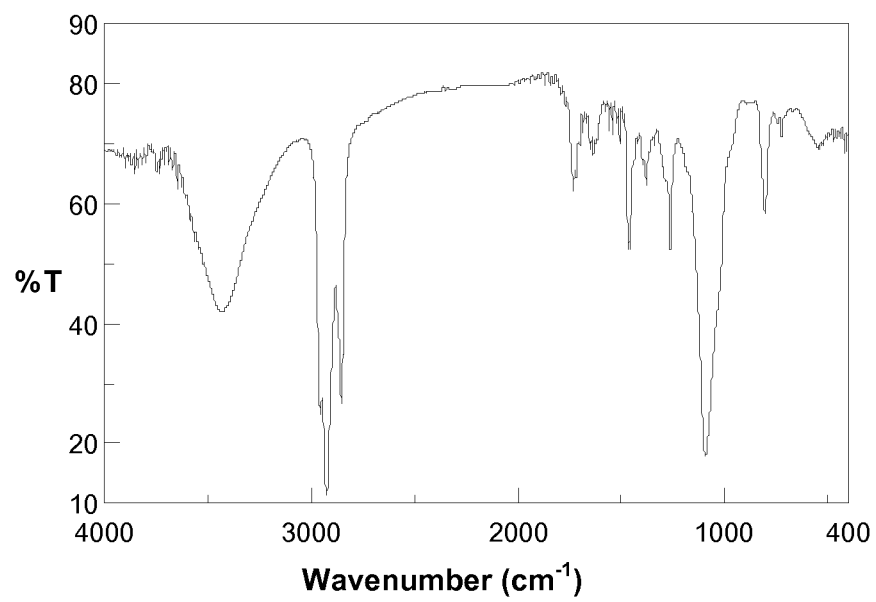
FIG. 1 is a graph for showing an IR spectrum of an octyl-etherified fullerene derivative.

An embodiment of the present invention is described in detail. However, the present invention is not limited to this embodiment.

A resin composition according to this embodiment contains a long-chain alkyl-etherified fullerene derivative. Now, first, the long-chain alkyl-etherified fullerene derivative (hereinafter sometimes abbreviated as "fullerene derivative") is described.

<Fullerene Derivative>

The fullerene derivative includes: a fullerene skeleton formed of a spherical shell-shaped carbon molecule; and a long-chain alkyl group having 4 or more carbon atoms, which is bonded to the fullerene skeleton through an ether bond.

In this embodiment, the "fullerene skeleton" is a generic term for skeletons formed of spherical shell-shaped carbon molecules. An example of the carbon molecule capable of forming a spherical shell-shaped molecule is a nanomaterial represented by the general formula Cn (where n represents an integer of 60 or more). Well-known examples of the number n for the fullerene skeleton include 60, 70, 76, 78, 80, 82, 84, 86, 88, 90, 92, and 96. Of those, n=60 is preferred from the viewpoint of an improvement in heat resistance.

It should be noted that the nanomaterial herein means a substance having at least a primary particle size which is less than 100 nm.

In addition, the alkyl ether in the fullerene derivative is bonded to the fullerene skeleton through an ether bond, and contains a long-chain alkyl group having 4 or more carbon atoms. As long as the fullerene derivative contains a long-chain alkyl group having 4 or more carbon atoms, the alkyl group may be any one of a linear chain and a branched chain. In addition, the alkyl group, which has 4 or more carbon atoms, preferably has 6 or more carbon atoms from the viewpoint of an improvement in compatibility with a resin, and the upper limit value of the number of carbon atoms is preferably 12.

In addition, a hydroxy group is preferably further bonded to the fullerene skeleton, as a group separate from the alkyl ether bond. This is because not only effects such as an antistatic effect and a dew condensation-preventing effect tend to be obtained by virtue of an amphiphilic property, but also the hydroxy group, which is bonded to the n-conjugated system of the fullerene and is weakly acidic, is considered to have a radical scavenging effect like hydroxy groups of polyphenols and hydroquinones as antioxidants, and thus a contribution tends to be made to the improvement in the heat resistance of the resin composition.

Further, the fullerene derivative preferably has, for example, a structure represented by the following general formula (1).

$$Cn[O(CH_2)xCH_3]y(OH)z \qquad (1)$$

(In the general formula (1), n represents 60 or more, x represents 3 or more, y represents 1 or more, and z represents 0 or a positive number of 1 or more.)

In the general formula (1), y+z is preferably from 8 to 14, and is more preferably from 10 to 12 in order to synthesize the fullerene derivative under simple conditions. For example, in the case of the total number of substituents y+z=10, y, which represents 1 or more, more preferably represents 5 or more and 9 or less from the viewpoints of dispersibility and the amphiphilic property. In addition, z, which represents 0 or a positive number of 1 or more, more preferably represents 1 or more and 5 or less from the viewpoints of the heat resistance and stability. Accordingly, the ratio of y to z (number of long-chain alkyl groups/number of hydroxy groups) is more preferably from 1/1 to 9/1 because with such ratio, a contribution tends to be made to the improvement in the heat resistance without the impairment of compatibility with the resin or any other advantage.

<Production Method for Fullerene Derivative>

As a production method for the fullerene derivative, for example, there is given a method including: a first step of synthesizing a polycyclosulfated fullerene (CS) from an untreated fullerene and fuming sulfuric acid; and a second step of synthesizing the long-chain alkyl-etherified fullerene derivative by introducing the long-chain alkyl group to the fullerene skeleton through the ether bond generated by allowing the polycyclosulfated fullerene (CS) to react with a long-chain alcohol.

In addition, in place of the polycyclosulfated fullerene (CS), there may be used any other fullerene derivative having a substituent, which is easily eliminated by a nucleophilic substitution reaction of an alcohol, such as a halogenated fullerene having any one of the fluorine, chlorine, and bromine atoms in a substituent on the fullerene skeleton or a nitrated fullerene having a nitro group. However, the method involving allowing the polycyclosulfated fullerene (CS) to react with the long-chain alcohol described above is preferred.

Before or after the first step and the second step, another step such as pretreatment or aftertreatment for the purpose of purification may be included.

<Resin Composition>

The resin composition containing the fullerene derivative is described.

First, the fullerene derivative to be used in the resin composition refers to the long-chain alkyl-etherified fullerene derivative described above.

Next, a crystalline thermoplastic resin, a non-crystalline thermoplastic resin, and a curable resin are each preferably used as a resin to be used in the resin composition because through the use of the fullerene derivative according to this embodiment, the heat resistance is improved more effectively than expected from the properties of the respective resins. One kind of those resins may be used alone, or two or more kinds thereof may be used in combination.

The crystalline thermoplastic resin is a thermoplastic resin that can be confirmed to have crystallinity by X-ray analysis, differential thermal analysis, or the like. Examples of such crystalline thermoplastic resin include: polyolefin-based resins such as polyethylene (PE)-based or polypropylene (PP)-based resins; polyester-based resins such as polyethylene terephthalate (PET) and polybutylene terephthalate (PBT); polyamide-based resins such as nylon 6 and nylon 66; a vinylidene chloride resin; a fluorine-based resin; and a polyacetal-based resin.

Examples of the non-crystalline thermoplastic resin include: acrylic resins of (meth)acrylic acid, (meth)acrylamide, (meth)acrylonitrile, and the like alone and copolymers thereof; styrene-based resins such as polystyrene, a styrene-acrylonitrile copolymer, and an acrylonitrile-butadiene-styrene resin (ABS resin); a polycarbonate-based resin; and vinyl-based resins of vinyl esters such as vinyl acetate and vinyl propionate, and derivatives of the vinyl-based resins (such as polyvinyl alcohol, polyvinyl formal, and an ethylene-vinyl acetate copolymer).

Examples of the curable resin include a phenol-based resin, an epoxy-based resin, a urethane-based resin, a melamine-based resin, a urea-based resin, and an alkyd-based resin.

Regarding a ratio between the contents of the fullerene derivative and the resin, the content of the fullerene derivative is preferably from 0.01 part by weight to 10 parts by weight with respect to 100 parts by weight of the resin. This is because: when the content of the fullerene derivative is excessively low, excellent heat resistance tends to be hardly exhibited; and when the content of the fullerene derivative is excessively high, the viscosity of the resin composition tends to be so high that the resin composition is difficult to mold.

In addition, in addition to the fullerene derivative and the resin, the resin composition according to this embodiment may further contain, for example: additives such as a plasticizer, a dispersant, an antioxidant, a heat stabilizer, a UV absorber, a weathering stabilizer, an antidripping agent, a release agent, a lubricant, a flame retardant, a coloring agent, an antibacterial agent, and an antistatic agent; and glass fibers, carbon fibers, high-melting point organic fibers, carbon black, silica, calcium carbonate, clay, talc, shirasu balloons, and glass balloons.

<Production Method for Resin Composition>

Any known method may be adopted as a production method for the resin composition according to this embodiment. Major examples thereof include a solvent method and melt-kneading. In particular, the solvent method is preferred because of its suitability for highly dispersing the fullerene derivative according to this embodiment.

Examples of the solvent method include: a method involving dissolving the fullerene derivative in a solvent, adding the solution to a molten resin, stirring and mixing the components with a blade stirrer, a homogenizer, a ball mill, or the like, and then removing the solvent by heat or the like; and a method involving mixing the fullerene derivative dissolved in a solvent and the resin, melting the mixture, stirring and mixing the molten components, and then removing the solvent by heat or the like.

In addition, an example of the melt-kneading is a method involving melting and kneading a mixture of the fullerene derivative and the resin with a kneader, a Banbury mixer, a roll, or the like.

Thus, the resin composition according to this embodiment is obtained. The resin composition can be suitably used in the form of a material obtained using the resin composition, such as a food packaging material, a molding material, an automobile-related material, an electrical and electronic equipment-related material, a building material, or an industrial machinery-related material.

EXAMPLES

The present invention is described below in detail by way of Examples. It should be noted that the scope of the present invention is not limited to Examples described below and various modifications may be made without departing from the gist of the present invention.

Example 1

Preparation of Long-Chain Alkyl-Etherified Fullerene Derivative

A fullerene ($C_{60}$) (trade name: NANOM PURPLE ST) as a raw material was purchased and prepared from Frontier Carbon Corporation.

The first step of synthesizing a polycyclosulfated fullerene (CS) was performed as described below in conformity with Reference Example 1 in Examples of JP-A-2005-251505.

5 g of the fullerene ($C_{60}$) was allowed to react with 75 mL of 60% fuming sulfuric acid under a nitrogen atmosphere at 60° C. under stirring for 3 days. Next, the resultant reaction product was added dropwise into 500 mL of diethyl ether in an ice bath to provide a precipitate. The resultant precipitate was separated by centrifugation. The separated product was washed with a total of about 1,000 mL of anhydrous diethyl ether divided into several portions, further washed with about 300 mL of a mixed solvent of diethyl ether/acetonitrile=2/1, and dried in a vacuum to provide a sample. The yield was 5.3 g.

An infrared absorption spectrum (IR spectrum) of the resultant sample was found to agree well with the infrared absorption spectrum (IR spectrum) of FIG. 1 of JP-A-2005-251505. Thus, the sample was identified as a polycyclosulfated fullerene (CS).

Next, the second step of synthesizing an octyl-etherified fullerene ($OctC_{60}$) was performed as described below.

1 g of the polycyclosulfated fullerene (CS) obtained in the foregoing was allowed to react with 10 mL of octyl alcohol under a nitrogen atmosphere at 80° C. under stirring for 3 days. The reaction product was washed with about 500 mL of water, and sulfuric acid in the product was removed until the pH of the washing water became 6.5. Next, a Kugelrohr apparatus (80° C., 10 mmHg or less) was used to remove unreacted octyl alcohol by vacuum distillation.

Further, silica gel column chromatographic treatment was performed with a mixed solvent of diethyl ether/methanol=40/60 as an eluent to provide an octyl-etherified fullerene ($OctC_{60}$).

The structure of the octyl-etherified fullerene ($OctC_{60}$) obtained in the foregoing was identified on the basis of infrared absorption spectrum measurement (IR spectrum) and nuclear magnetic resonance measurement ($^1$H-NMR spectrum), and its structural formula was determined to be $C_{60}[O(CH_2)_7CH_3]_7(OH)_3 \cdot 3H_2O$ on the basis of the content of water estimated by elemental analysis measurement and thermogravimetric analysis. Thus, the octyl-etherified fullerene ($OctC_{60}$) was identified.

It should be noted that the infrared absorption spectrum measurement was performed by a KBr method using FT/IR-300E manufactured by JASCO Corporation. The result of the measurement is shown in FIG. 1. In FIG. 1, strong absorption attributed to C—H stretching vibration was observed at around 2,900 cm$^{-1}$ and strong absorption attributed to C—O stretching vibration was observed at around 1,100 cm$^{-1}$, which suggested the presence of an octyl ether group. In addition, broad absorption attributed to O—H stretching vibration was observed at around 3,400 cm$^{-1}$, which suggested the presence of a hydroxy group.

Figure 2:
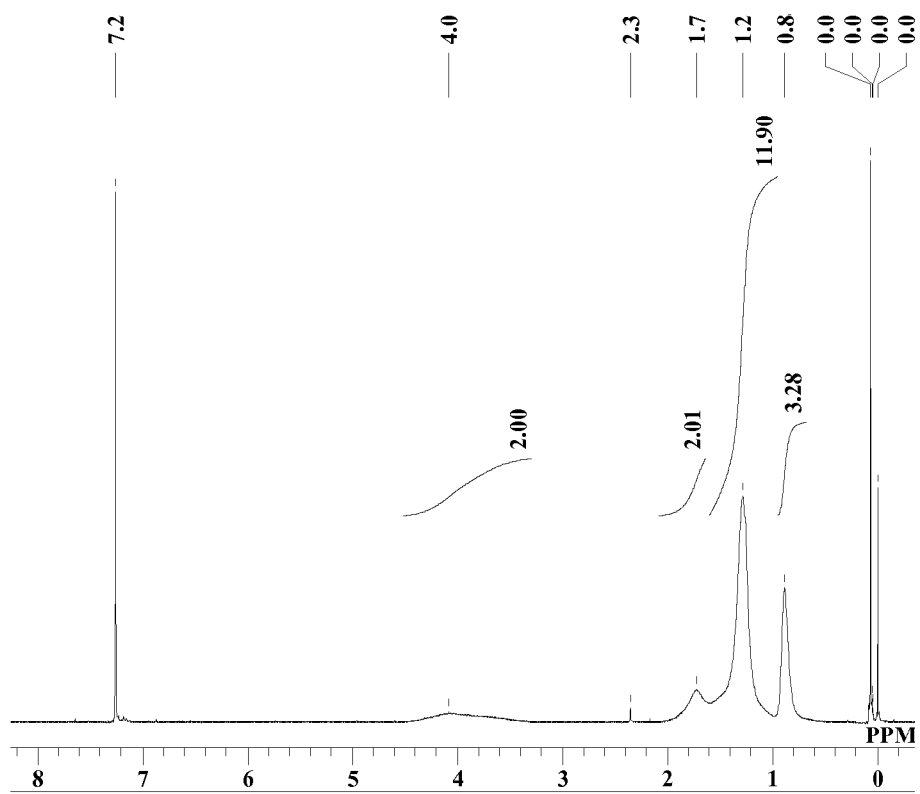
FIG. 2 is a graph for showing a $^1$H-NMR spectrum of an octyl-etherified fullerene derivative.

In addition, the nuclear magnetic resonance measurement was performed using JNM-EX270 manufactured by JEOL Ltd. at 270 MHz in $CDCl_3$. The result of the measurement is shown in FIG. 2. In FIG. 2, absorption corresponding to each of the three kinds of protons of an octyl ether group ($CH^a_3$—$(CH^b_2)_6$—$(CH^c_2)$—O—) ($H^a$=0.8 ppm, $H^b$=1.2 ppm, $H^c$=4.1 ppm; $H^a$:$H^b$:$H^c$=3:12:2) was observed, which confirmed the introduction of an octyl ether group. It should be noted that protons derived from water and the hydroxy group were observed at around 1.7 ppm.

Further, the elemental analysis measurement was performed using Micro Corder JM10 manufactured by J-Science Lab CO., Ltd. The results of the measurement are shown in Table 1 below.

TABLE 1

Structural formula determination of $C_{60}[O(CH_2)_7CH_3]y(OH)z \cdot mH_2O$

| | | Element | | | | | | |
|---|---|---|---|---|---|---|---|---|
| | | C | H | N | $H_2O$ | | | |
| | | | | Unit | | | | |
| | | % | % | % | wt % | y | z | m |
| $OctC_{60}$ | Analysis value | 79.88 | 7.47 | 0.05 | 3.8 | — | — | — |
| | Calculated value | 80.50 | 7.46 | 0 | 3.1 | 7 | 3 | 3 |

When the structural formula is represented by $C_{60}[O(CH_2)_7CH_3]y(OH)z \cdot mH_2O$, y, z, and m are found to be 7, 3, and 3, respectively, on the basis of the elemental analysis values and calculated values in Table 1 above. Thus, the structural formula of $OctC_{60}$ is found to be $C_{60}[O(CH_2)_7CH_3]_7(OH)_3 \cdot 3H_2O$.

<Preparation of Resin Composition>

An octyl-etherified fullerene derivative/polypropylene nanocomposite ($OctC_{60}$/PP) as a resin composition containing the octyl-etherified fullerene derivative ($OctC_{60}$) was produced as described below.

5 mg of the octyl-etherified fullerene derivative ($OctC_{60}$) obtained in the foregoing was dissolved in 0.5 mL of o-xylene, the solution was added to 1,000 mg of polypropylene (PP), and the components were dissolved and mixed at 150° C. Further, o-xylene was removed by evaporation on a hot plate at from 150° C. to 170° C. Thus, a solid sample 1 was obtained.

Heat resistance measurement (TGA measurement) was performed using a thermogravimetric apparatus (manufactured by Shimadzu Corporation, DTA-50). The TGA measurement was performed under an air atmosphere under the conditions of a sample weight of about 4 mg, a measurement temperature of from 30° C. to 600° C., and a rate of temperature increase of 10° C./min. Thus, a temperature at which the solid sample 1 lost 10 wt % of its weight (temperature at a weight loss of 10 wt %) was determined. The temperature at a weight loss of 10 wt % was used as an indicator to evaluate heat resistance. The results of the evaluation are shown in Table 2 below and FIG. 3.

The solid sample 1 had a temperature at a weight loss of 10 wt % of 282° C.

Example 2

In a manner similar to that of Example 1, 10 mg of the octyl-etherified fullerene derivative ($OctC_{60}$) was dissolved in 0.5 mL of o-xylene, the solution was added to 1,000 mg of polypropylene (PP), and the components were dissolved and mixed at 150° C. Further, o-xylene was removed by evaporation on a hot plate at from 150° C. to 170° C. Thus, a solid sample 2 was obtained. The heat resistance of the solid sample 2 was evaluated in the same manner as in Example 1.

The solid sample 2 had a temperature at a weight loss of 10 wt % of 289° C.

Example 3

In a manner similar to that of Example 1, 30 mg of the octyl-etherified fullerene derivative ($OctC_{60}$) was dissolved in 0.5 mL of o-xylene, the solution was added to 1,000 mg of polypropylene (PP), and the components were dissolved and mixed at 150° C. Further, o-xylene was removed by evaporation on a hot plate at from 150° C. to 170° C. Thus, a solid sample 3 was obtained. The heat resistance of the solid sample 3 was evaluated in the same manner as in Example 1.

The solid sample 3 had a temperature at a weight loss of 10 wt % of 307° C.

Example 4

In a manner similar to that of Example 1, a butyl-etherified fullerene derivative ($ButC_{60}$) was synthesized as described below.

In the first step, a polycyclosulfated fullerene (CS) was synthesized in the same manner as in Example 1.

In the second step, 1 g of the polycyclosulfated fullerene (CS) was allowed to react with 10 mL of butyl alcohol under a nitrogen atmosphere at 80° C. under stirring for 3 days. The reaction product was washed with about 500 mL of water, and sulfuric acid in the product was removed until the pH of the washing water became 6.5. Next, silica gel column chromatography treatment was performed with ethyl acetate as an eluent to provide a butyl-etherified fullerene derivative ($ButC_{60}$).

Next, in a manner similar to that of Example 1, 10 mg of the butyl-etherified fullerene derivative ($ButC_{60}$) was dissolved in 0.5 mL of o-xylene, the solution was added to 1,000 mg of polypropylene (PP), and the components were dissolved and mixed at 150° C. Further, o-xylene was removed by evaporation on a hot plate at from 150° C. to 170° C. Thus, a solid sample 4 was obtained. The heat resistance of the solid sample 4 was evaluated in the same manner as in Example 1.

The solid sample 4 had a temperature at a weight loss of 10 wt % of 270° C.

Comparative Example 1

A solid comparative sample 1 was produced in the same manner as in Example 1 except that no octyl-etherified fullerene derivative ($OctC_{60}$) was added. The heat resistance of the solid comparative sample 1 was evaluated in the same manner as in Example 1.

The solid comparative sample 1 had a temperature at a weight loss of 10 wt % of 259° C.

Comparative Example 2

A solid comparative sample 2 was produced in the same manner as in Example 1 except that a fullerene ($C_{60}$) was added in place of the octyl-etherified fullerene derivative ($OctC_{60}$). The heat resistance of the solid comparative sample 2 was evaluated in the same manner as in Example 1.

The solid comparative sample 2 had a temperature at a weight loss of 10 wt % of 259° C.

Comparative Example 3

In a manner similar to that of Example 1, an ethyl-etherified fullerene derivative ($EtoC_{60}$) was synthesized as described below.

In the first step, a polycyclosulfated fullerene (CS) was synthesized in the same manner as in Example 1.

In the second step, 1 g of the polycyclosulfated fullerene (CS) was allowed to react with 10 mL of ethyl alcohol under a nitrogen atmosphere at 80° C. under stirring for 3 days. The reaction product was washed with about 500 mL of water, and sulfuric acid in the product was removed until the pH of the washing water became 6.5. Next, silica gel column chromatography treatment was performed with ethyl acetate as an eluent to provide an ethyl-etherified fullerene derivative ($EtoC_{60}$).

Next, in a manner similar to that of Example 1, 10 mg of the ethyl-etherified fullerene derivative ($EtoC_{60}$) was dissolved in 0.5 mL of o-xylene, the solution was added to 1,000 mg of polypropylene (PP), and the components were dissolved and mixed at 150° C. Further, o-xylene was removed by evaporation on a hot plate at from 150° C. to 170° C. Thus, a solid comparative sample 3 was obtained. The heat resistance of the solid comparative sample 3 was evaluated in the same manner as in Example 1.

The solid comparative sample 3 had a temperature at a weight loss of 10 wt % of 262° C.

TABLE 2

| | Fullerene derivative | | | | Heat resistance (° C.)[b] | Difference in heat resistance from blank (° C.)[c] |
|---|---|---|---|---|---|---|
| | Alkyl group | Presence or absence of $C_{60}$ | Content (wt %)[a] | Resin | | |
| Example 1 | Octyl group | $C_{60}$ | 0.5 | PP | 282 | 23 |
| Example 2 | Octyl group | $C_{60}$ | 1.0 | PP | 289 | 30 |
| Example 3 | Octyl group | $C_{60}$ | 3.0 | PP | 307 | 48 |
| Example 4 | Butyl group | $C_{60}$ | 1.0 | PP | 270 | 11 |
| Comparative Example 1 | — | — | 0 | PP | 259 | — |
| Comparative Example 2 | — | $C_{60}$ | 0.5 | PP | 259 | 0 |
| Comparative Example 3 | Ethyl group | $C_{60}$ | 1.0 | PP | 262 | 3 |

[a]A weight ratio with respect to the resin
[b]In the case of PP, a temperature at a weight loss of 10 wt % in TGA measurement (under the atmosphere, rate of temperature increase: 10° C./min)
[c]A difference from the temperature at a weight loss of 10 wt % of Comparative Example 1 formed only of the resin with no fullerene derivative added As understood from the results of Table 2 above, in each of Examples 1 to 4, the difference in heat resistance from Comparative Example 1 (blank) formed only of the resin with no fullerene derivative added was 10° C. or more. Thus, it was found that the heat resistance was distinctly improved. In contrast, in each of Comparative Example 2 having added thereto the untreated fullerene, and Comparative Example 3 having added thereto the ethyl-etherified fullerene derivative, the difference in heat resistance from the blank was from 0° C. to 3° C. Thus, it was found that the heat resistance was hardly improved.

In addition, a comparison among Examples 2 and 4, and Comparative Example 3, each having the same fullerene content (1.0 wt %) and using the same resin (PP), showed that the heat resistance was found to be hardly improved when the alkyl group bonded through an ether bond was an ethyl group having 2 carbon atoms (Comparative Example 3), whereas Examples 2 and 4 each showed a high improvement in heat resistance. Those results revealed that when the alkyl group bonded to the fullerene derivative through an ether bond was a long-chain alkyl group having 4 or more carbon atoms, the compatibility of the fullerene derivative with the resin was improved, and as a result, a resin composition having excellent heat resistance was obtained.

In addition, in order to confirm whether a similar effect was shown also in the case of a resin different from that in the foregoing, the same experiment as that described above except for using linear low-density polyethylene (LLDPE) in place of the polypropylene (PP) was performed. The results of the experiment are shown in Table 3 below.

Example 5

In a manner similar to that of Example 1, 5 mg of the octyl-etherified fullerene derivative ($OctC_{60}$) was dissolved in 0.5 mL of o-xylene, the solution was added to 1,000 mg of the linear low-density polyethylene (LLDPE), and the components were dissolved and mixed at 150° C. Further, o-xylene was removed by evaporation on a hot plate at from 150° C. to 170° C. Thus, a solid sample 5 was obtained. The heat resistance of the solid sample 5 was evaluated in the same manner as in Example 1.

The solid sample 5 had a temperature at a weight loss of 20 wt % of 397° C.

Example 6

In a manner similar to that of Example 1, 30 mg of the octyl-etherified fullerene derivative ($OctC_{60}$) was dissolved in 0.5 mL of o-xylene, the solution was added to 1,000 mg of the linear low-density polyethylene (LLDPE), and the components were dissolved and mixed at 150° C. Further, o-xylene was removed by evaporation on a hot plate at from 150° C. to 170° C. Thus, a solid sample 6 was obtained. The heat resistance of the solid sample 6 was evaluated in the same manner as in Example 1.

The solid sample 6 had a temperature at a weight loss of 20 wt % of 397° C.

Comparative Example 4

A solid comparative sample 4 was produced in the same manner as in Example 5 except that no octyl-etherified fullerene derivative ($OctC_{60}$) was added. The heat resistance of the solid comparative sample 4 was evaluated in the same manner as in Example 5.

The solid comparative sample 4 had a temperature at a weight loss of 20 wt % of 349° C.

Comparative Example 5

A solid comparative sample 5 was produced in the same manner as in Example 5 except that a fullerene ($C_{60}$) was added in place of the octyl-etherified fullerene derivative ($OctC_{60}$). The heat resistance of the solid comparative sample 5 was evaluated in the same manner as in Example 5.

The solid comparative sample 5 had a temperature at a weight loss of 20 wt % of 350° C.

TABLE 3

| | Fullerene derivative | | | | Difference in heat |
| | Alkyl group | Presence or absence of $C_{60}$ | Content (wt %)[d] | Resin | Heat resistance (° C.)[e] | resistance from blank (° C.)[f] |
|---|---|---|---|---|---|---|
| Example 5 | Octyl group | $C_{60}$ | 0.5 | LLDPE | 397 | 48 |
| Example 6 | Octyl group | $C_{60}$ | 3.0 | LLDPE | 397 | 48 |
| Comparative Example 4 | — | — | 0 | LLDPE | 349 | — |
| Comparative Example 5 | — | $C_{60}$ | 0.5 | LLDPE | 350 | 1 |

[d]A weight ratio with respect to the resin
[e]In the case of LLDPE, a temperature at a weight loss of 20 wt % in TGA measurement (under the atmosphere, rate of temperature increase: 10° C./min)
[f]A difference from the temperature at a weight loss of 20 wt % of Comparative Example 4 formed only of the resin with no fullerene derivative added As understood from the results of Table 3 above, in each of Examples 5 and 6, the difference in heat resistance from Comparative Example 4 (blank) formed only of the resin with no fullerene derivative added was 40° C. or more. Thus, it was found that the heat resistance was distinctly improved as in Examples 1 to 4. In contrast, in Comparative Example 5 having added thereto the untreated fullerene, the difference in heat resistance from the blank was 1° C. Thus, it was found that the heat resistance was hardly improved.

As described above, even when the polypropylene (PP) of Examples 1 to 4 was changed to the linear low-density polyethylene (LLDPE) of Examples 5 and 6, the heat resistance was found to be improved as in Examples 1 to 4. Thus, it was found that a similar tendency was shown also in the case of a different resin.

Although specific embodiments of the present invention have been described in Examples above, Examples are for illustrative purposes only and are not to be construed as limitative. It is intended that various modifications apparent to a person skilled in the art fall within the scope of the present invention.

The resin composition according to this embodiment can be advantageously utilized in each of the following various applications: food packaging materials, molding materials, automobile-related materials, electrical and electronic equipment-related materials, building materials, and industrial machinery-related materials.

What is claimed is:

1. A long-chain alkyl-etherified fullerene derivative, comprising:
   a fullerene skeleton formed of a spherical shell-shaped carbon molecule; and
   a long-chain alkyl group having 4 or more carbon atoms which is bonded to the fullerene skeleton through an ether bond.

2. The long-chain alkyl-etherified fullerene derivative according to claim 1, further comprising a hydroxy group which is bonded to the fullerene skeleton.

3. The long-chain alkyl-etherified fullerene derivative according to claim 2, wherein a ratio (y/z) of a number y of the long-chain alkyl groups to a number z of the hydroxy groups is from 1/1 to 9/1.

4. A production method for the long-chain alkyl-etherified fullerene derivative of claim 1, comprising:
   synthesizing a polycyclosulfated fullerene from a fullerene and fuming sulfuric acid; and
   synthesizing the long-chain alkyl-etherified fullerene derivative by introducing the long-chain alkyl group to the fullerene skeleton through the ether bond generated by reacting the polycyclosulfated fullerene with a long-chain alcohol.

5. A resin composition, comprising:
   a resin; and
   the long-chain alkyl-etherified fullerene derivative of claim 1.

6. The resin composition according to claim 5, wherein a content of the long-chain alkyl-etherified fullerene derivative is from 0.01 part by weight to 10 parts by weight with respect to 100 parts by weight of the resin.

7. The resin composition according to claim 5, wherein the resin comprises at least one resin selected from the group consisting of a crystalline thermoplastic resin, a non-crystalline thermoplastic resin, and a curable resin.

* * * * *